United States Patent [19]

Mullins

[11] Patent Number: 4,870,203
[45] Date of Patent: Sep. 26, 1989

[54] PREPARATION OF GEMINAL DICARBAMATES

[75] Inventor: Michael J. Mullins, Midland, Mich.

[73] Assignee: The Dow Chemical Company, Midland, Mich.

[21] Appl. No.: 899,131

[22] Filed: Aug. 21, 1986

Related U.S. Application Data

[63] Continuation-in-part of Ser. No. 682,643, Dec. 17, 1984, abandoned.

[51] Int. Cl.$^4$ ............... C07C 125/073; C07C 125/075

[52] U.S. Cl. ..................................... 560/158; 560/25; 560/137

[58] Field of Search ......................... 560/158, 25, 137

[56] References Cited

PUBLICATIONS

Furukawa, J. Org. Chem., 23, pp. 672–676 (1958).

Primary Examiner—Michael L. Shippen

[57] ABSTRACT

Prepare $\alpha, \beta$-saturated geminal biscarbamates by contacting an $\alpha,\beta$-unsaturated ether with a carbamate under reaction conditions, optionally in the presence of a catalyst.

25 Claims, No Drawings

PREPARATION OF GEMINAL DICARBAMATES

CROSS-REFERENCE TO RELATED APPLICATION

This application is a continuation-in-part of Ser. No. 682,643, filed Dec. 17, 1984, now abandoned.

BACKGROUND OF THE INVENTION

The present invention relates to the production of geminal dicarbamates.

Compounds having carbamate moieties are useful in that they can be converted to the corresponding isocyanates via known methods. For example, U.S. Pat. No. 4,388,246 discloses a method of thermally cleaving dicarbamates to form diisocyanates.

It has long been known that aldehydes but not simple ketones condense with carbamates directly to give geminal biscarbamates. See, e.g., *J. Org. Chem.*, V. 10, pp. 145-8 (1941). It is also known to react aldehydes with unsaturated carbamates, e.g., $H_2C=CH-CH_2-O-CONH_2$, to form geminal di(unsaturated) dicarbamates. U.S. Pat. Nos. 2,384,074; and 2,385,911. These synthetic techniques are of limited usefulness in that they can only be used to synthesize products having a hydrogen on the geminal carbon atom.

Joseph Hoch, in Vol. 210, *Academie Sci. Compt. Rendu.*, pp. 560-2 (1935), teaches the preparation of isopropylidene-bis-(ethyl carbamate) in unspecified yield by reacting urethane (ethyl carbamate, $H_2NCO_2C_2H_5$) with 2,2-diethoxypropane at from 105° C.–190° C., optionally in the presence of aniline chlorohydrate. Thus, this technique produced a geminal dicarbamate not having a hydrogen atom on the geminal carbon atom. However, it is disclosed that yield is reduced in the absence of aniline chlorohydrate.

It would be desirable to have a new, simple method for the high yield production of a large class of geminal dicarbamates, including compounds which do not have a hydrogen on the geminal carbon atom. Heretofore, such a method has not been disclosed.

SUMMARY OF THE INVENTION

The present invention is a new synthetic method for the production of $\alpha,\beta$-saturated geminal dicarbamates in high yield. The process involves contacting an $\alpha,\beta$-unsaturated ether with a carbamate, optionally in the presence of an acid catalyst, under reaction conditions such that an $\alpha,\beta$-saturated geminal dicarbamate is formed. One equivalent of a geminal ether is produced as a coproduct. Surprisingly, the process produces $\alpha,\beta$-saturated geminal dicarbamates in high yield using an unsaturated ether as one of the starting materials. The geminal dicarbamates are useful in that they can be thermally cracked to form isocyanates. The geminal diethers can be thermally cracked to form alcohols and unsaturated ethers.

DETAILED DESCRIPTION OF THE INVENTION

The process of the present invention requires an $\alpha,\beta$-unsaturated ether, and a carbamate. An acid catalyst and a solvent independently are optionally employed.

Ethers having $\alpha,\beta$-olefinic unsaturation advantageously are employed in the process of the present invention. For the purposes of the present invention, the term "$\alpha,\beta$-unsaturated" refers to olefinic unsaturation between the carbon atom bonded to the ether oxygen atom, i.e., the alpha carbon atom, and a carbon atom bonded thereto. Examples of typical $\alpha,\beta$-unsaturated ethers include diisopropenyl ether, isopropenyl methyl ether, phenyl isopropenyl ether, $\alpha$-methoxy styrene, $\alpha$-ethoxy styrene and the like. Preferred unsaturated ethers are represented by the formula

wherein each R, $R_a$ and $R_b$ is independently H, aliphatic or aromatic; and wherein $R_c$ is aliphatic or aromatic. Preferably, R and $R_a$ are independently hydrogen or alkyl, and $R_b$ and $R_c$ are alkyl. Most preferably, R and $R_a$ are H or lower alkyl, and $R_b$ and $R_c$ are lower alkyl. For the purposes of the present invention, the term "lower alkyl" refers to alkyl moieties of from 1 to about 4 carbon atoms. For the purposes of the present invention, the terms "aliphatic" and "aromatic" include moieties having atoms such as halogen atoms, O, S, and N.

A carbamate advantageously is employed in the process of the present invention. Examples of typical carbamates include methyl carbamate, ethyl carbamate, propyl carbamate, n-butyl carbamate, sec-butyl carbamate, benzyl carbamate, phenyl carbamate and the like. Preferred carbamates are represented by the formula

wherein $R_e$ is aliphatic or aromatic. Preferably, $R_e$ is alkyl. Most preferably, $R_e$ is lower alkyl. In the process of the present invention, the carbamate and the unsaturated ether can be employed in any amount sufficient for the reaction to proceed to yield at least one geminal dicarbamate. Typically, from about 0.5 to about 2 moles of carbamate are employed per mole of unsaturated ether. Preferably, from about 0.9 to about 1.05 moles of carbamate are employed per mole of unsaturated ether. Most preferably, a stoichiometric ratio is employed.

An acid catalyst optionally can be employed in the process of the present invention, and preferably an acid catalyst is employed. Examples of typical acid catalysts include organic acids such as sulfonic or carboxylic acids, inorganic acids such as mineral acids, Lewis acids such as zinc chloride, aluminum chloride, or boron trifluoride, solid acids such as silica gels, acidic clays, aluminas, zeolites, and polymeric acids such as sulfonated polystyrene resins. Examples of preferred catalysts include sulfonic acids and sulfonated resins. Typically, a catalytic amount of the catalyst is employed. Preferably, from about 0.0001 to about 0.01 equivalents of catalyst are employed per mole of carbamate reactant; most preferably, from about 0.0005 to about 0.002 equivalents are employed.

A solvent optionally can be employed in the process of the present invention, and preferably a solvent is employed. The solvent can be any inert material in which the carbamate and unsaturated ether are soluble. Typical solvents include, for example, chlorinated and nonchlorinated hydrocarbons such as methylene chloride, toluene, xylenes, dichlorobenzenes, chlorinated ethanes, and aliphatic, aromatic, or mixed aromatic-aliphatic ethers. Methylene chloride is the preferred solvent. While the solvent can be employed in any amount which solubilizes the reactants, the solvent typically is employed in amounts ranging from about 0.1 to about 10 liters of solvent per kg of reactants. Preferably, from about 0.5 to about 2 liters of solvent are employed per kg of reactants. Mixtures of solvents can be employed.

The reaction can be conducted at any combination of temperature and pressure at which the reaction proceeds to form a geminal dicarbamate. The reaction typically is conducted at from about −30° C. to about 200° C.; preferably is conducted at from about −10° C. to about 100° C.; and most preferably is conducted at a temperature of from about 0° C. to about 25° C. Advantageously, the process temperature is below the boiling point of the reaction mixture, although the process can be conducted at reflux temperature. The process pressure can be sub- or superatmospheric. Preferably, and for the sake of convenience, the process is conducted at ambient pressure.

When the carbamate and α,β-unsaturated ether are combined under the conditions previously described herein, an α,β-saturated geminal dicarbamate is produced. Preferred α,β-saturated geminal dicarbamates are represented generally by the formula:

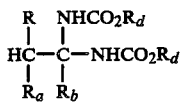
(II)

wherein each $R_d$ is independently aliphatic or aromatic, and wherein R, $R_a$, and $R_b$ are as defined hereinabove. Preferably, each $R_d$ is independently alkyl. Most preferably, each $R_d$ is independently lower alkyl. The most preferred geminal dicarbamate is 2,2-N,N-bis(methyl carbamato)propane. The process of the present invention is advantageous in that it can produce a wide variety of α,β-saturated geminal dicarbamates in unexpectedly high yields. Preferably, the yield of α,β-saturated geminal dicarbamate is at least about 90 percent. For the purposes of the present invention, the term "yield" refers to the numerical product of conversion of the carbamate and selectivity to the geminal dicarbamate. The α,β-saturated geminal dicarbamates can be recovered using known techniques such as crystallization or distillation.

The process of the present invention produces a geminal diether in addition to the geminal dicarbamate. Preferred geminal diethers are represented generally by the formula:

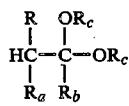
(IV)

wherein R, $R_a$, $R_b$, and $R_c$ are as defined hereinabove. Preferably, the geminal carbamate and geminal diether are produced in approximately equimolar amounts.

SPECIFIC EMBODIMENTS

The following examples are intended to illustrate the invention and should not be construed as limiting its scope.

EXAMPLE 1

Synthesis of 2,2-N,N-bis(ethyl carbamato)propane

A solution of ethyl carbamate (8.91 g, 100 mmoles) in 40 ml of methylene chloride is added to 15 mg of p-toluene sulfonic acid in a 100-ml round-bottom flask equipped with a stirring means. The mixture is cooled with ice water under a nitrogen atmosphere. Isopropenyl methyl ether (14 ml, density 0.765 g/ml, 131 mmoles) is added to the mixture over a period of about 20 minutes. The mixture is then allowed to stand for 20 minutes. The resulting colorless solution is washed twice using 10 ml of saturated NaHCO₃ solution each time, and then is washed twice using 10 ml of water each time. The washed solution is dried with magnesium sulfate, and is filtered and evaporated to remove the methylene chloride and 2,2-dimethoxy propane, leaving 10.56 g of white crystals having a melting point of 98.5° C. to 100° C.

The yield of crude product is 97 percent calculated as follows: 100 mmoles of ethyl carbamate+131 mmoles of isopropenyl methyl ether reacts to form 10.56 g of the named product (10.56 g÷218 g/mole=0.04844 mole=48.44 mmoles). The ethyl carbamate conversion is 100 percent. Since, theoretically, 2 moles of ethyl carbamate is required per mole of product, the yield is: (100 percent conversion)(2×48.44 mmoles)/(100 mmoles ethyl carbamate)=96.88≈97 percent. Recrystallization of the white crystals using toluene gives crystals having a melting point of 107° C. to 108° C. Spectral analyses (proton and carbon nuclear magnetic resonance, infrared, and mass spectroscopy) are consistent with the assigned structure.

EXAMPLE 2

Synthesis of 2,2-N,N-bis(methyl carbamato)propane

The procedure of Example 1 is repeated with the following exceptions: ethyl carbamate is replaced with methyl carbamate (6.66 g, 88.7 mmoles); 35 ml of methylene chloride is employed; 38 mg of p-toluene sulfonic acid is employed; and 10.7 ml of isopropenyl methyl ether is employed. The initial white crystals weigh 7.99 g and have a melting point of 103° C. to 106° C. The yield is 94 percent. The white crystals are recrystallized from toluene to give crystals having a melting point of 122° C. to 123° C. Spectral analyses are consistent with the assigned structure.

The preceding examples demonstrate the high yield production of geminal dicarbamates which do not have a hydrogen atom on the geminal carbon atom.

What is claimed is:

1. A process for the preparation of α,β-saturated geminal dicarbamates, comprising contacting an α,β-unsaturated ether of the formula:

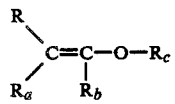

wherein each R, $R_a$ and $R_b$ is independently H, aliphatic or aromatic, and wherein $R_c$ is aliphatic or aromatic; with a carbamate represented by the formula:

wherein $R_e$ is independently aliphatic or aromatic; at a temperature of no more than about 25° C. and under reaction conditions such that there are formed a geminal diether of the formula:

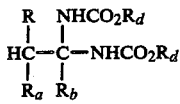

and a geminal dicarbamate of the formula:

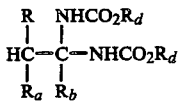

wherein said $R_d$ is independently aliphatic or aromatic.

2. The process of claim 1 wherein the contacting is performed in the presence of an inert solvent.

3. The process of claim 1 wherein the temperature is no less than about $-30°$ C.

4. The process of claim 1 wherein $R_b$ is aliphatic or aromatic.

5. The process of claim 1 wherein the temperature is no less than about $-10°$ C.

6. The process of claim 1 wherein the contacting is in the presence of an acid catalyst.

7. The process of claim 1 wherein R and $R_a$ are H.

8. The process of claim 1 wherein $R_b$ is H.

9. The process of claim 1 wherein $R_c$ is lower alkyl.

10. A process for the preparation of $\alpha,\beta$-saturated tertiary geminal dicarbamates comprising contacting a carbamate of the formula:

$$H_2NCO_2R_e$$

wherein $R_e$ is independently aliphatic or aromatic, with an $\alpha,\beta$-unsaturated ether represented by the formula:

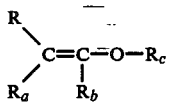

wherein R and $R_a$ are independently H, aliphatic or aromatic, and wherein $R_b$ and $R_c$ are independently aliphatic or aromatic, in the presence of an acid catalyst at no more than about 25° C. and under reaction conditions such that there is formed an $\alpha,\beta$-saturated tertiary geminal dicarbamate having the formula:

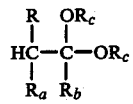

wherein each $R_d$ is independently aliphatic or aromatic.

11. A process of claim 10 wherein $R_b$ is alkyl.

12. A process of claim 11 wherein R and $R_a$ are independently H or alkyl.

13. A process of claim 12 wherein each $R_d$ is independently alkyl.

14. A process of claim 13 wherein R and $R_a$ are independently H or lower alkyl, and wherein $R_b$ and $R_c$ are independently lower alkyl.

15. A process of claim 14 wherein R and $R_a$ are H, and $R_b$ and $R_d$ are methyl.

16. A process of claim 14 wherein R and $R_a$ are H, $R_b$ is methyl, and $R_d$ is ethyl.

17. A process of claim 10 wherein $R_c$ is alkyl.

18. A process of claim 10 wherein $R_c$ is lower alkyl.

19. A process of claim 10 wherein the temperature is no less than about $-10°$ C.

20. A process of claim 10 wherein p-toluene sulfonic acid is employed as a catalyst.

21. A process of claim 10 wherein an inert solvent is employed.

22. A process of claim 21 wherein the solvent is methylene chloride.

23. A process comprising contacting an $\alpha,\beta$-unsaturated ether with a carbamate in the presence of an acid catalyst under reaction conditions such that there is formed in a yield, based on the carbamate, of at least about 90 percent an $\alpha,\beta$-saturated geminal dicarbamate of the formula:

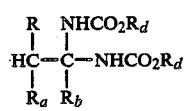

wherein R, $R_a$ and $R_b$ are independently H, aliphatic or aromatic, and $R_d$ is aliphatic or aromatic.

24. The process of claim 1 wherein the temperature of the reaction is maintained at no less than about 0° C.

25. A process of claim 10 wherein the temperature of the reaction is no less than about 0° C.

* * * * *

UNITED STATES PATENT AND TRADEMARK OFFICE
CERTIFICATE OF CORRECTION

PATENT NO. : 4,870,203

DATED : September 26, 1989

INVENTOR(S) : Michael J. Mullins

It is certified that error appears in the above-identified patent and that said Letters Patent is hereby corrected as shown below:

Column 4, line 23, "= 96.88 ~ 97 percent" should read -- = 96.88 ≅ 97 percent -- .

Column 5, at the top, the formula should correctly read --

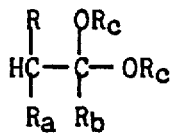

Column 6, at the top, the formula should correctly read --

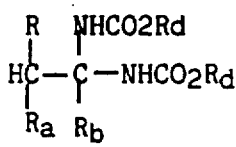

Signed and Sealed this

Sixth Day of November, 1990

Attest:

HARRY F. MANBECK, JR.

*Attesting Officer*     *Commissioner of Patents and Trademarks*